United States Patent [19]

Ruyle

[11] Patent Number: 4,584,294

[45] Date of Patent: Apr. 22, 1986

[54] FUSED TRICYCLIC LACTAMS AS ANGIOTENSIN CONVERTING ENZYME INHIBITORS AND AS ANTIHYPERTENSIVE AGENTS

[75] Inventor: William V. Ruyle, Scotch Plains, N.J.

[73] Assignee: Merck & Co., Inc., Rahway, N.J.

[21] Appl. No.: 669,179

[22] Filed: Nov. 7, 1984

[51] Int. Cl.$^4$ .................... A61K 31/55; C07D 223/32
[52] U.S. Cl. ................................... 514/214; 568/328; 260/239.3 T
[58] Field of Search ................. 260/239.3 T; 514/214; 568/328

[56] References Cited

U.S. PATENT DOCUMENTS 4,410,520 10/1983 Watthey ..................... 260/239.3 B
4,415,496 11/1983 Harris et al. ................ 260/239.3 B

*Primary Examiner*—Robert T. Bond
*Attorney, Agent, or Firm*—Salvatore C. Mitri; Michael C. Sudol

[57] ABSTRACT

The invention relates to fused tricyclic lactams and related compounds which are useful as angiotensin converting enzyme inhibitors and as antihypertensives.

8 Claims, No Drawings

FUSED TRICYCLIC LACTAMS AS ANGIOTENSIN CONVERTING ENZYME INHIBITORS AND AS ANTIHYPERTENSIVE AGENTS

BACKGROUND OF INVENTION

This invention relates to fused tricyclic lactams and derivatives thereof which are useful as angiotensin converting enzyme inhibitors and as antihypertensives.

U.S. Pat. No. 4,410,520 discloses benzofused bicyclic lactams which are useful as angiotensin converting enzyme (ACE) inhibitors and U.S. Pat. No. 4,415,496 discloses bicyclic lactams which are also useful as ACE inhibitors and wherein the five membered ring contains a sulfur atom. Neither of these patents suggests the tricyclic lactam compounds of this invention nor that such compounds would be useful as ACE inhibitors and as antihypertensives.

SUMMARY OF THE INVENTION

It has now been found that the tricyclic lactam compounds of this invention and derivatives thereof are potent ACE inhibitors and are thus useful when administered, alone or in combination with another antihypertensive compound and/or diuretic compound and/or a calcium entry blocker, to treat diseases responsive to the inhibition of angiotensin converting enzyme; e.g., hypertension, congestive heart failure, and the like.

DETAILED DESCRIPTION OF THE INVENTION

This invention relates to tricyclic lactam compounds and derivatives thereof which are useful as angiotensin converting enzyme (ACE) inhibitors and as antihypertensive agents. The tricyclic lactam compounds of this invention are represented by the general formula:

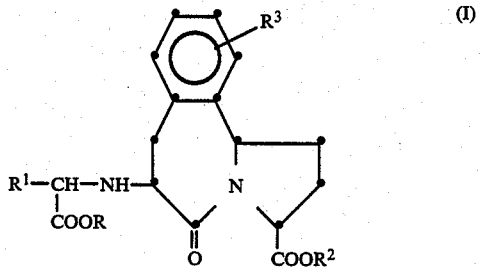

wherein:
R and $R^2$ are independently
(a) hydrogen;
(b) $C_1$–$C_6$ alkyl;
(c) substituted $C_1$–$C_6$ alkyl wherein the substituents are hydroxy, $C_1$–$C_4$ alkyloxy and di-($C_1$–$C_4$)-alkylamino;
(d) $C_6$ or $C_{10}$ aryl;
(e) substituted $C_6$ or $C_{10}$ aryl wherein the substituents are $C_1$–$C_6$ alkyl, halo (F, Cl, Br, I), and $C_1$–$C_4$ alkyloxy;
(f) hetero ($C_6$ or $C_{10}$) aryl wherein the heteroatom can be one of O, N or S;
(g) substituted hetero ($C_6$ or $C_{10}$) aryl or substituted hetero ($C_6$ or $C_{10}$) aryloxy wherein the heteroatom can be one of O, N or S and the substituents are $C_1$–$C_6$ alkyl, halo (F, Br, Cl, I) and $C_1$–$C_4$ alkyloxy;
$R^1$ is
(a) hydrogen;
(b) $C_1$–$C_8$ straight or branched alkyl;
(c) $C_2$–$C_8$ straight or branched alkenyl;
(d) $C_2$–$C_8$ straight or branched alkynyl;
(e) $C_3$–$C_{10}$ cycloalkyl;
(f) $C_6$ or $C_{10}$ aryl ($C_1$–$C_4$) alkyl;
(g) substituted $C_1$–$C_8$ alkyl which can optionally contain an O, S, S=O, O=S=O, C=O, $CONR_2$, $SO_2NR_2$, NRCO, $NRCONR_2$, $OCONR_2$, NRCOO or $-NR_2$ group wherein R is as defined above and wherein there can be 1-3 substituents selected from halo (F, Br, Cl, I), carboxamido, $C_1$–$C_4$ alkoxy carbonyl, mercapto, amino, and R wherein R is as defined above;
$R^3$ is
(a) hydrogen;
(b) halo (F, Br, Cl, I);
(c) $C_1$–$C_6$ alkyl;
(d) $C_1$–$C_6$ alkyloxy; and,
the pharmaceutically acceptable salts thereof.

The alkyl groups are represented by such groups as, for example, methyl, vinyl, propargyl, butenyl, isobutyl, and the like.

The cycloalkyl groups include, for example, cyclobutyl, cyclopentyl, cyclohexenyl, and the like.

The aryl groups include phenyl, naphthyl, indenyl, biphenyl and benzofused cycloalkyl groups such as, for example, indanyl and 1,2,3,4-tetrahydronaphthyl.

Heteroaryl groups include such compounds as, for example, pyridyl, thienyl, furyl, imidazolyl and thiazolyl as well as any bicyclic group in which any of the above heterocyclic rings is fused to another aromatic or heterocyclic ring such as, for example, indolyl, quinolinyl, isoquinolinyl, benzimidozolyl, 1,5-naphthyridyl and quinoxalinyl.

Preferred are those compounds of Formula I wherein:
R and $R^2$ are independently
(a) hydrogen;
(b) $C_1$–$C_6$ alkyl;
(c) substituted $C_1$–$C_6$ alkyl wherein the substituents are hydroxy, $C_1$–$C_4$ alkyloxy and di-($C_1$–$C_4$)-alkylamino;
$R^1$ is
(a) hydrogen;
(b) $C_1$–$C_8$ straight or branched alkyl;
(c) $C_2$–$C_8$ straight or branched alkenyl;
(d) $C_2$–$C_8$ straight or branched alkynyl;
(e) $C_3$–$C_{10}$ cycloalkyl;
(f) $C_6$ or $C_{10}$ aryl ($C_1$–$C_4$) alkyl;
(g) substituted $C_1$–$C_8$ alkyl which can optionally contain an O, S, C=O, $CONR_2$, or $-NR_2$ group wherein R is as defined above and wherein there can be 1-3 substituents selected from halo, carboxamido, $C_1$–$C_4$ alkoxy carbonyl, mercapto, amino, and R wherein R is as defined above;
$R^3$ is
(a) hydrogen;
(b) halo (F, Br, Cl, I);
(c) $C_1$–$C_6$ alkyl;
(d) $C_1$–$C_6$ alkyloxy.

The compounds of Formula I can be prepared by the processes shown in the Reaction Scheme hereinbelow wherein R-$R^3$ are as defined above unless otherwise indicated.

As will be evident to those skilled in the art and as demonstrated in the Examples which follow, reactive groups not involved in the reactions, such as amino, carboxy, mercapto, etc., may be protected by methods standard in peptide chemistry prior to the coupling reactions and subsequently deprotected by conventional means to obtain the desired products.
Reaction Scheme
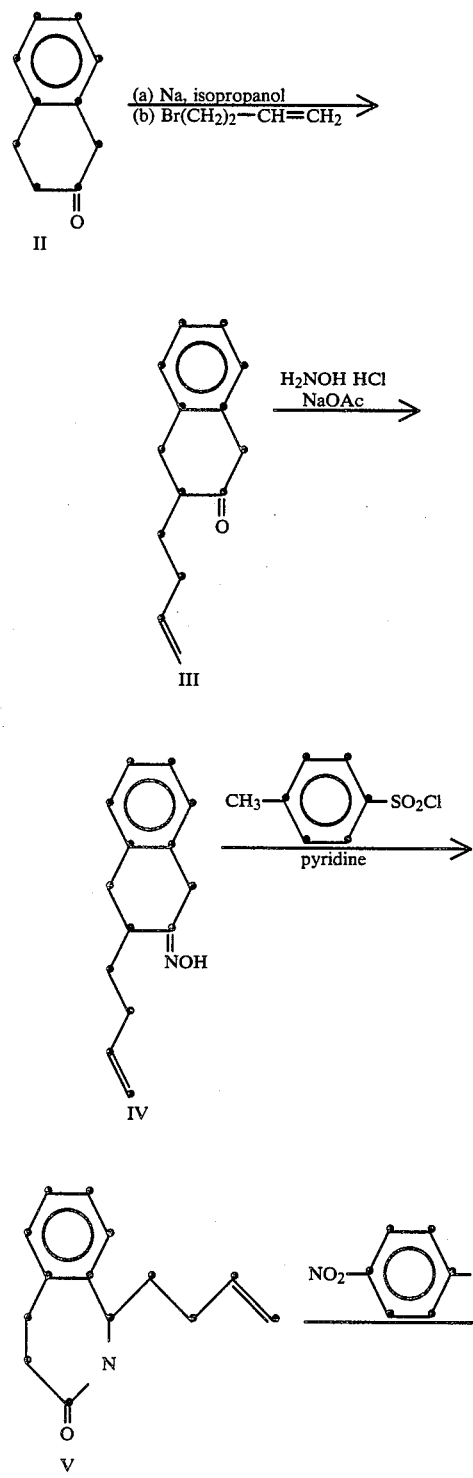
-continued
Reaction Scheme
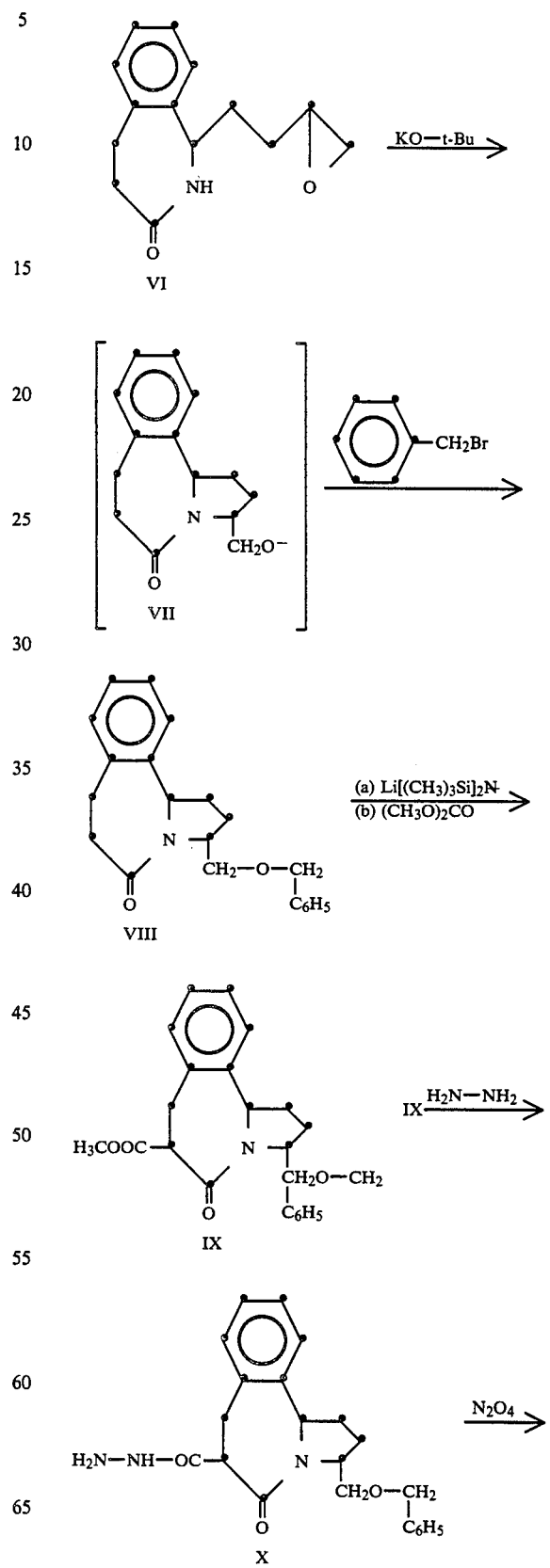

-continued
Reaction Scheme
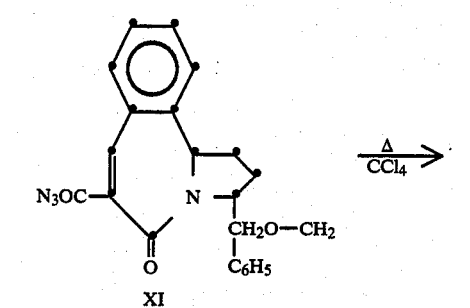
XI
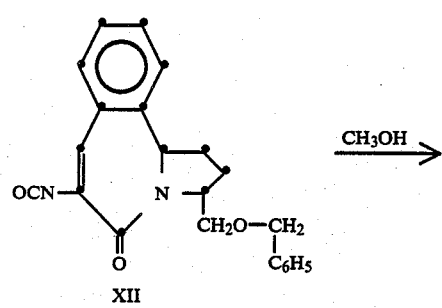
XII
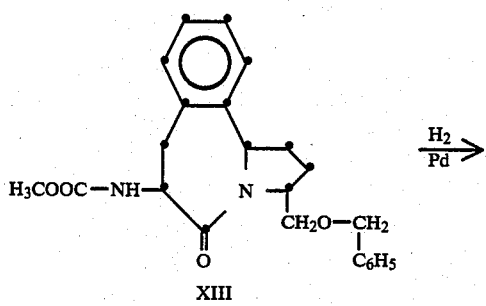
XIII
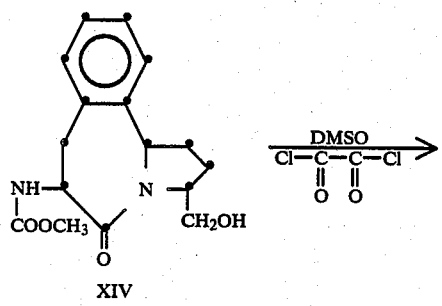
XIV
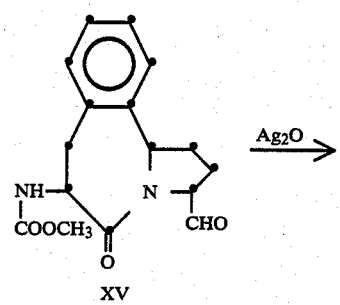
XV
-continued
Reaction Scheme
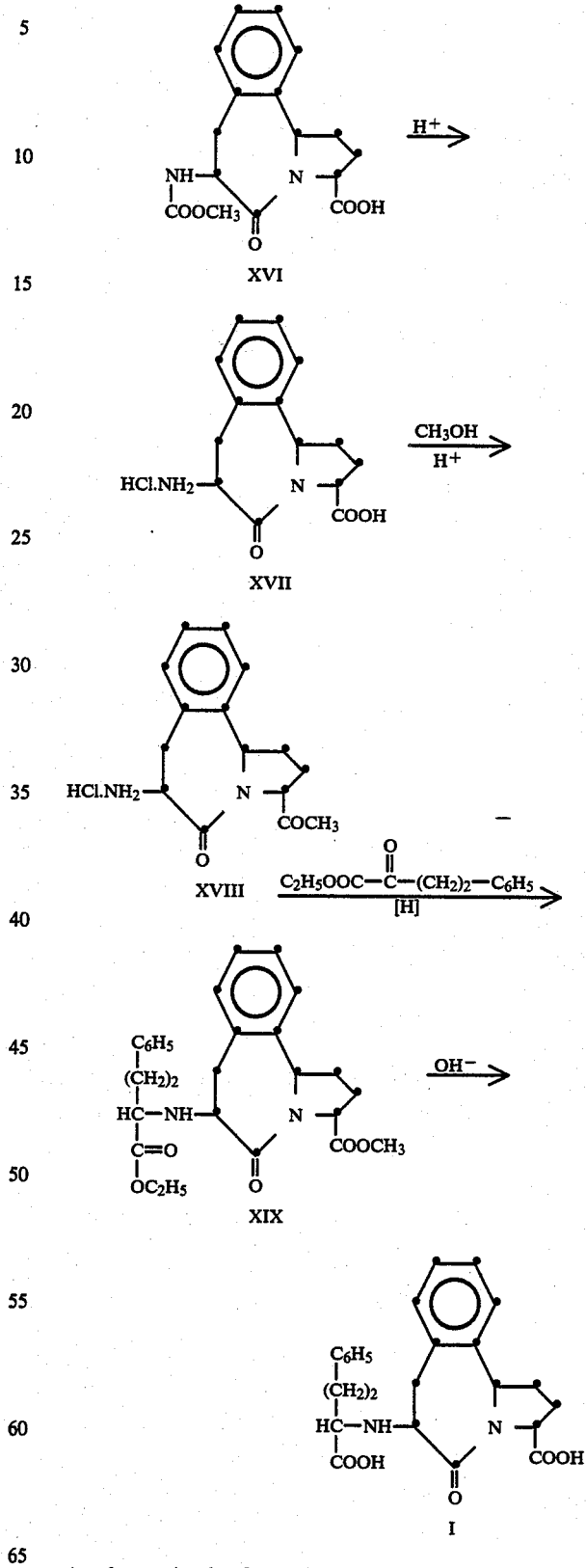
As shown in the foregoing Reaction Scheme, commercially obtained 2-tetralone II is alkylated in the presence of sodium, isopropanol and a haloolefin to obtain vinyl compound III which, upon treatment with an hydroxylamine, is converted to oxime IV. By means of Beckmann Rearrangment [E. Beckmann, Ber., 19, 988 (1886)], oxime IV is converted to 7-membered lactam V which is then oxidized with p-benzoic acid to obtain epoxide VII. Upon treatment with potassium-t-butoxy, epoxide VI is cyclized to tricyclic product VII which is treated without isolation with benzobromide to afford benzyloxy VIII. Benzyloxy VIII is then treated with a strong base followed by treatment with dimethylcarbonate to afford tricyclic methoxy carbonyl IX which, upon treatment with hydrazine yields unsaturated hydrazide X. Treatment of hydrazide X with dinitrogen tetraoxide affords unsaturated azide XI [O. E. Edwards, et al., *Can. J. Chem.*, 55, 371 (1977)] which is then heated and treated with carbon tetrachloride according to the Curtius Reaction [*Organic Reactions*, 3, 337 (1946)] to afford unsaturated isocyanate XII. Isocyanate XII is treated with methanol to obtain unsaturated carbamate XIII which is treated with hydrogen in the presence of palladium catalyst to obtain hydroxyl XIV. Oxidation of hydroxyl XIV by treatment with dimethylsulfoxide (DMSO) in the presence of oxalyl affords aldehyde XV which, upon treatment with silver oxide, yields acid XVI. When treated with a strong acid, XVI is hydrolyzed to amine XVII. Amine XVII is then treated with methanol in the presence of a strong acid to obtain amino ester XVIII which is treated with a keto ester under reducing conditions to obtain tricyclic XIX. Tricyclic XIX is then hydrolyzed in the presence of a base to afford a compound I of the invention.

The final stages in these syntheses are to separate the desired diastereomers by chromatography or crystallization and to remove protecting groups, if present, by standard means. When diesters of Formula I in which $R=R^2$ are desired, they can be prepared from, for example, diacids of I ($R=R^2=H$) using the desired alcohols under anhydrous acidic conditions.

Preferred diastereomers are isolated by chromatography or crystallization of intermediates or the end products or their salts. One can also resolve intermediates by the use of optically active salts or bases. Finally, if desired, compounds of this invention can also be employed as a mixture of their enantiomers or diastereomers.

The α-keto acids or α-keto esters utilized in the process of the invention are known in the art or can be made by numerous, known methods. For example, synthons such as

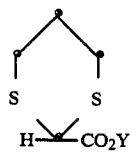

can be converted to α-keto acids or esters using methods involving alkylation followed by hydrolysis as described in the literature. An excellent method involves the reaction of Grignard reagents $R_1MgX$ with $ClCOCO_2Y$ or $YO_2CCCO_2Y$. Another method involves condensing substituted acetic acid esters with diethyl oxalate followed by hydrolytic decarboxylation under acidic conditions to obtain α-keto acids. Carefully controlled acid hydrolysis in alcohol of acyl cyanides, which are prepared from acid chlorides and cuprous cyanide, also proves to be a viable synthetic route to α-keto esters. Nucleophilic displacement reactions on chloro or bromo pyruvic acid (ester) can also be used to produce a variety of interesting α-keto acids (esters). In these formulae, Y is a group such as loweralkyl or benzyl and protecting groups are employed as necessary in the $R_1$ group if interfering functionality is present.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases e.g., dicyclohexylamine salts, N-methyl-D-glucamine, salts with amino acids like arginine, lysine and the like. Also salts with organic and inorganic acids can be prepared, e.g., HCl, HBr, $H_2SO_4$, $H_3PO_4$, methanesulfonic, toluenesulfonic, maleic, fumaric, camphorsulfonic. The non-toxic physiologically acceptable salts are preferred, although other salts are also useful, e.g., in isolating or purifying the product.

The salts can be formed by conventional means as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The compounds of this invention inhibit angiotensin converting enzyme and thus block conversion of the decapeptide angiotensin I to angiotensin II. Angiotensin II is a potent pressor substance. Thus, blood-pressure lowering can result from inhibition of its biosynthesis especially in animals and humans whose hypertension is angiotensin II related. Furthermore, converting-enzyme degrades the vasodepressor substance, bradykinin. Therefore, inhibitors of angiotensin converting enzyme may lower blood-pressure also by potentiation of bradykinin. Although the relative importance of these and other possible mechanisms remains to be established, inhibitors of angiotensin converting enzyme are effective antihypertensive agents in a variety of animal models and are useful clinically, for example, in many human patients with renovascular, malignant and essential hypertension. See, for example, D. W. Cushman et al., *Biochemistry* 16, 5484 (1977).

The evaluation of converting enzyme inhibitors is guided by in vitro enzyme inhibition assays. For example, a useful method is that of Y. Piquilloud, A. Reinharz and M. Roth, *Biochem. Biophys. Acta*, 206, N36 (1970) in which the hydrolysis of carbobenzyloxy-phenylalanylhistidinylleucine is measured. In vivo evaluations may be made, for example, in normotensive rats challenged with angiotension I by the technique of J. R. Weeks and J. A. Jones, *Proc. Soc. Exp. Biol. Med.*, 104, 646 (1960) or in a high renin rat model such as that of S. Koletsky et al., *Proc. Soc. Exp. Biol. Med.* 125, 96 (1967).

Thus, the compounds of this invention are useful as antihypertensives in treating hypertensive mammals, including humans, and they can be utilized to achieve the reduction of blood pressure by formulating them in appropriate compositions for administration. The compounds of this invention can be administered to patients in need of such treatment in a dosage range of 0.5 to 100 mg per patient generally given several times a day, thus giving a total daily dose of from 0.5 to 400 mg per day. The dose will vary depending on severity of disease, weight of patient and other factors which a person skilled in the art will recognize.

Thus, in accordance with the present invention there is provided a pharmaceutical composition for inhibiting angiotensin converting enzyme or treating hypertension comprising a pharmaceutically acceptable carrier and a pharmaceutically effective amount of a compound of Formula I.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid (3) binding agents such as starch, or gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be (1) suspending agents such as sodium carboxymethylcellulose, methylcellulose, hydroxypropylmethylcellulose, sodium alginate, polyvinylpyrrolidone, gum tragacanth and gum acacia;

(2) dispersing or wetting agents which may (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example; polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In additon, sterile, fixed oils are conventionally employed as a solvent or suspending medium. For this purpose any bland fixed oil may be employed including synthetic mono- or diglycerides. In additon, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

The amount of active ingredient that may be combined with the carrier materials to produce a single dosage form will vary depending upon the host treated and the particular mode of administration. For example, a formulation intended for oral administration may contain from 5 mg to 5 gm of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of this invention can also be administered in combination with other antihypertensives and/or diuretics and/or calcium entry blockers. For example, the compounds of this invention can be given in combination with such compounds as acetazolamide, amiloride, aminophylline, atenolol, bendroflumethiazide, benzthiazide, bumetanide, chorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)-ethyl]amino]-3-[4-(2-thienyl)-1H-imidazol-2-yl]-phenoxy]-2-propanol, thacrynic acid, flumethiazide, furosemide, guanethidene sulfate, hydralazine hydrochloride, hydrochlorothiazide, hydroflumethiazide, (+)-4-[3-[-[2-(1-hydroxycyclohexyl) ethyl]-4-oxo-2-thiazolidinyl]-propyl]-benzoic acid, indacrinone and variable ratios of its enantiomers, merethoxylline procaine, methylclothiazide, methyldopa, methldopate hydrochloride, metolazone, metoprolol tartate, minoxidil, naldolol, nifedipine, pargyline hydrochloride, pindolol, polythiazide, prazosin, propranolol, quinethazone, *rauwolfia serpentina*, rescinnamine, reserpine, sodium ethacrynate, sodium nitroprusside, spironolactone, ticrynafen, timolol, triamterene, trichlormethiazide, trimethophan camsylate, bepridil, diltiazim, etafenone, falipamil, felodipine, flunarizine, gallopamil, indapamide, lidoflazine, nicardipine, nifedipine, nimopidine, nitrendipine, perhexiline, prenylamine, tiapamil, verapamil, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the antihypertensives of this invention effective in the 0.5 to 1000 mg per day range can be effectively combined with the following compounds at the indicated per day dose range: hydrochlorothiazide (10–100 mg); chlorothiazide (125–2000 mg); manipulated indacrinone enantiomer ratio (25–150 mg); ethacrynic acid (15–2000 mg); amiloride (5–20 mg); furosemide (5–80 mg); propranolol (20–480 mg); timolol (5–60 mg); and methyldopa (65–2000 mg); and the pivaloyloxyethyl ester of methyldopa (30–1000 mg). In addition, triple drug combinations of hydrochlorothiazide (10–100 mg) plus amiloride (5–20 mg) plus converting enzyme inhibitor of this invention (0.5–1000 mg); hydrochlorothiazide (10–100 mg) plus timolol (5–20 mg) plus the converting enzyme inhibitor of this invention (0.5–1000 mg); or manipulated indacrinone enantiomer ratio (25–150 mg) plus amiloride (5–20 mg) plus converting enzyme inhibitor of this invention (0.5–1000 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

The following examples are illustrative of the invention and constitute especially preferred embodiments. The preferred diastereomers of these examples are isolated by conventional column chromatography or fractional crystallization. Unless otherwise indicated, all temperatures are in degrees Celsius.

EXAMPLE 1

1-(But-3-ene-yl)-2-tetralone

Sodium metal, (1.26 g, 0.055 mole) was dissolved in 40 ml isopropanol under nitrogen atmosphere at reflux temperature. After cooling slightly, 8.0 g (0.055 mole) of 2-tetralone was added, followed by 1-bromo-4-butene, (10.5 g, 0.078 mole) after which the mixture was heated at reflux for 2 hours. The reaction mixture was cooled, and diluted to 200 ml with water. The pH was brought to 3 by the addition of 6N HCl. The foregoing procedures were all carried out under nitrogen atmosphere. The mixture was extracted 3 times with 50 ml portions of ether, the organic extract washed with excess sodium bicarbonate solution, dried over magnesium sulfate, and concentrated in vacuo to an oil. Yield 11.25 g.

This crude product was stirred with 50 ml of saturated aqueous sodium bisulfite solution for 30 minutes. The solid which formed was filtered and washed well with ether. This solid was essentially the pure adduct of sodium bisulfite and 2-tetralone.

The filtrate from the bisulfate adduct was extracted with ether, and the concentrated extract was chromatographed on 800 ml of silica gel, (E. Merck No. 60). Elution with hexane-ethyl acetate 6:1, yielded 1,1-bis(-but-4-ene-yl)-2-tetralone, 1.83 g; 1-(but-4-ene-yl)-2-tetralone, 5.69 g; and 2-tetralone, 0.65 g. The structures of the substituted tetralones were confirmed by NMR and mass spectrometry.

EXAMPLE 2

1-(But-3-ene-yl)-2-oximino-tetralin

A mixture of 5.43 g of 1-(but-3-ene-yl)-2-tetralone, 54 ml of methanol, 2.06 g of hydroxylamine hydrochloride, and 2.41 g of sodium acetate was stirred and heated at reflux for 20 minutes. The reaction mixture was concentrated in vacuo to a small volume and the residue partitioned between ether and water. The ether layer was washed with sodium bicarbonate solution, dried over anhydrous magnesium sulfate, and concentrated to an oil, 5.78 g.

The crude product was chromatographed on a column of 500 ml of silica gel, (E. Merck, No. 60) from which it was eluted with hexane-ethyl acetate, 4:1. The desired oxime (3.89 g, 67%) was obtained as a colorless oil which showed a single spot on TLC.

Anal: Calc'd for $C_{14}H_{17}NO$: C, 78.10; H, 7.96; N, 6.51. Found: C, 77.68; H, 7.83; N, 6.34.

EXAMPLE 3

7-(But-4-ene-yl)-5,6-Benzperhydroazepine-2-one

A solution of 3.8 g (0.0176 mole) of 1-(but-4-ene-yl)-2-oximino tetralin in 3.5 ml. of dry pyridine was stirred in an ice bath while 5.05 g. (0.0266 mole) of p-toluenesulfonyl chloride was added gradually. The reaction mixture was kept at 5° overnight after which 5 g of ice was added and the resulting solution concentrated in vacuo to a syrup. The syrup was partitioned between methylene chloride and a slight excess of 1N hydrochloric acid. The organic layer was washed with water, dried over magnesium sulfate and concentrated. The resulting solid was triturated with hexane-ether, 2:1 and filtered. Yield 3.30 g. This crude product was purified by chromatography on 300 ml of silica gel (E. Merck No. 60). Elution with ethyl acetate-hexane, 4:1 yielded 2.85 g (75%) of white needles, m.p. 112°-113°.

Anal. Calc'd for $C_{14}H_{17}NO$: C, 78.10; H, 7.96; N, 6.51. Found: C, 78.05; H, 7.92; N, 6.36.
NMR ($CDCl_3$) spectrum was consistent with the proposed structure. TLC; single spot.

EXAMPLE 4

7-(3,4-Epoxybutyl)-5,6-benzoperhydoazepine-2-one

A solution of 2.85 g (0.0132 mole) of 7-(but-3-ene-yl)-5,6-benzoperhydroazepine-2-one in 40 ml of methylene chloride was cooled to 0° and 3.53 g (0.0165 mole based on 85% purity) of technical p-nitro perbenzoic acid was added in portions during 20 minutes. The reaction mixture was stirred at room temperature overnight. After cooling to 15°, the mixture was filtered and the filtrate was washed four times with 15 ml portions of 10% sodium carbonate solution. The sodium carbonate extracts were back-washed with methylene chloride. The combined methylene chloride extracts were dried over magnesium sulfate and concentrated in vacuo to a colorless glass. The NMR spectrum ($CDCl_3$) showed the absence of olefinic protons. This material was used in the next Example (5) without further purification.

EXAMPLE 5

(8,9)-Benzo-3-(benzyloxymethyl)-octahydropyrrolo[1,2-a]azepine-5-one

The entire amount of product from Example 4, assumed to be about 0.013 mole, was dissolved in 20 ml of tetrahydrofuran. To this solution there was added, during a period of 5 minutes, 16.3 ml of a 1.0M solution of potassium t-butoxide in tetrahydrofuran. The reaction mixture was stirred at room temperature for 3.5 hours.

To the resulting dark solution there was added 2.48 g (0.0145 mole) of benzyl bromide in 5 ml of tetrahydrofuran during 15 minutes. After stirring at room temperature for 18 hours, 50 ml of ether, 7 ml of saturated aqueous ammonium chloride and sufficient water to dissolve the inorganic salts were added and the layers separated. The aqueous layer was extracted with 25 ml of ether and the combined ether extracts were washed with water followed by drying over magnesium sulfate. After concentration in vacuo, 4.16 g (quant.) of brown oil was obtained.

This crude material was chromatrographed on 400 ml of silica gel (E. Merck, No. 60). Elution with ethyl acetate yielded two main fractions:

A., "less polar fraction": 1.27 g (27%), m.p. 75°-80°
Anal: Calc'd for $C_{21}H_{23}NO_2$: C, 78.47; H, 7.21; N, 4.36. Found: C, 77.99; H, 6.93, N, 4.16.

B., "more polar fraction": 1.76 g (42%), m.p. 95°-97°

Anal: Calc'd for $C_{21}H_{23}NO_2$: C, 78.47; H, 7.21; N, 4.36. Found: C, 78.23; H, 7.21; N, 4.10.

A sample of fraction B was crystallized from aqueous ethanol by slow evaporation. Analysis of the resulting prisms by single crystal X-ray diffraction showed that the protons at positions 3 and 10 were in the "cis" relationship to each other. Accordingly, fraction A must be the corresponding "trans" isomer. Both fractions A and B are racemates.

EXAMPLE 6

(8,9)-Benzo-3-(benzyloxymethyl)-6-(carbomethoxy)octahydropyrollo[1,2-a]azepine-5-one While stirring under nitrogen and cooling in an ice bath, 12 ml (0.012 mole) of 1M lithium bis (trimethylsilyl)amide in hexane was added to 5.5 ml of tetrahydrofuran via a syringe. The resulting solution was cooled to −65° and a solution of 1.61 g of the "cis" racemate B from Example 5 in 9 ml of tetrahydrofuran was added dropwise by means of a syringe. After stirring at −65° for 0.5 hour, dimethyl carbonate (1.3 ml, 0.0155 mole) was added. The mixture was stirred at −65° for 1 hour, at 0° for 1 hour, and at room temperature for 0.5 hour. Saturated ammonium chloride solution, (9.5 ml) was then added followed by just enough water (ca. 2 ml) to dissolve the inorganic salts which were present. The aqueous layer was extracted with 2×5 ml of tetrahydrofuran and the combined tetrahydrofuran extracts concentrated in vacuo to an oil. This oil was taken up in 40 ml of ether and washed with 20 ml of 0.2N HCl. A solid material remained insoluble. The ether layer was separated, the solid was dissolved in chloroform, and the layers were separated. Concentration of the ether and chloroform layers and trituration with a small volume of ether yielded a total of 1.2 g of a solid which showed a single spot with thin layer chromatography (TLC). Recrystallization from ethyl acetate-hexane furnished prisms, m.p. 128°-129°.

Anal: Calc'd for $C_{23}H_{25}NO_4$: C, 72.80; H, 6.64; N, 3.69. Found: C, 72.40; H, 6.67; N, 3.61.

EXAMPLE 7

(8,9)-Benzo-3-(benzyloxymethyl)-6-(hydrazinocarbonyl)octahydropyrollo[1,2-a]azepine-5-one A mixture of 1.10 g of the methyl ester from Example 6, 10 ml of methanol and 1.5 ml of 97% hydrazine were heated at reflux for 1 hour and then concentrated to an oil in vacuo. The residue was partitioned between methylene chloride and water and the organic layer washed with aqueous 5% monosodium phosphate, dried over anhydrous magnesium sulfate, and concentrated in vacuo to a glass. Yield: 1.01 g. This material was used without purification in Example 8 below.

EXAMPLE 8

(8,9)-Benzo-3-(benzyloxymethyl)-6-(acetamido)-2,3,4,5,8,9-hexahydropyrollo[1,2-a]azepine-5-one.

The hydrazide from Example 7 (1.0 g, 0.0026 mole) was dissolved in 25 ml of carbon tetrachloride and cooled with stirring in an ice bath while 2.2 ml of a 1.5 ml solution of dinitrogen tetroxide in carbon tetrachloride was added dropwise. After stirring an additional 15 minutes in the ice bath, 1 ml of 1.5 M ammonium sulfamate was added. Methylene chloride (40 ml) was added to dissolve the oily product which separated. The organic layer was drawn off, washed with water, and concentrated in vacuo to a brown oil (1.1 g). The infrared (IR) spectrum (neat film) showed a strong peak at 2150 cm$^{-1}$ corresponding to the azide function. This material was suspended in 10 ml of carbon tetrachloride and heated at reflux for 2 hours. The resulting dark solution was decanted from a small amount of tarry material, treated with charcoal, and concentrated in vacuo to a reddish-brown glass, 0.95 g. The IR spectrum showed a peak at 2220 cm$^{-1}$ corresponding to the isocyanate function. The material was heated at reflux with 10 ml of methanol for 1.5 hour. The reaction mixture was concentrated and the residue chromatographed on 100 ml of silica gel. Elution with ethyl acetatehexane (1:1) furnished 0.37 g of orange oil. This oil was taken up in 3 ml of ether and hexane was cautiously added to precipitate a red gum. The supernatant was decanted and allowed to partially evaporate. A total of 70 mg of crystals were harvested from the supernatant. All mother liquors from this preparation were combined and chromatographed on silica gel. Elution with ether gave a cleaner separation than the ethyl acetate-hexane used previously; 110 mg of crystalline product was obtained which was identical with the 70 mg of the same crystalline product obtained earlier. The total yield, 180 mg, was 17.5% of theoretical from the hydrazide of Example 7. Recrystallization from chloroform-hexane furnished prisms, m.p. 110°–111°.

Anal Calc'd for $C_{23}H_{24}N_2O_4$: C, 70.39; H, 6.16; N, 7.14. Found: C, 70.06; H, 6.11; N, 6.94.

Mass Spec. M+392, U.V $\lambda_{Max}^{MeOH}$ 288 m$\mu$, 9300.

EXAMPLE 9

(8,9)-Benzo-3-(hydroxymethyl)-6-(acetamido)octahydropyrollo[1,2-a]azepine-5-one

A mixture containing 196 mg of the olefinic compound obtained in Example 8, 25 ml of methanol, 0.7 ml of N HCl in methanol, and 0.1 g of 10% Pd on carbon was stirred under hydrogen atmosphere until the uptake of hydrogen stopped. Approximately two moles of hydrogen per mole of substrate were taken up. The catalyst (Pd/C) was removed by filtration and the filtrate concentrated in vacuo to a foam. Trituration with ether furnished 114 mg (75%) of product, m.p. 160°–161°.

Anal: Calc'd for $C_{16}H_{20}N_2O_4$: C, 63.14; H, 6.62; N, 9.21. Found: C, 63.12; H, 6.81; N, 8.81.

A sample of product was recrystallized from methanol-water for single crystal X-ray analysis which showed that the methine protons at positions 3, 6, and 10 were in the "cis" relationship to one another.

EXAMPLE 10

(8,9)-Benzo-3-formyl-6-(acetamido)-octahydropyrollo[1,2-a]azepine-5-one

A solution of 0.607 ml of oxalyl chloride in 14.5 ml. of methylene chloride was stirred at $-65°$ while a solution of 1.05 ml of dimethyl sulfoxide in 3 ml of methylene chloride were added dropwise. The temperature of the mixture was brought to $-10°$ and kept there while a solution of 1.46 g of the hydroxy methyl compound obtained in Example 9 in 6 ml of methylene chloride and 0.5 ml of dimethyl sulfoxide were added during 3 minutes. After stirring an additional 15 minutes, 4.3 ml of triethylamine were added. The mixture was stirred at room temperature for 20 minutes and then shaken with 35 ml of water. The organic layer was separated and washed with saturated sodium chloride solution. After drying over magnesium sulfate, the solution was concentrated to a syrup which was triturated with ether to obtain 0.94 g of crystals.

Mass Spec. M+ 302. NMR (CDCl$_3$) 9.40 $\delta$(aldehyde proton); remainder of spectrum consistent with structure.

EXAMPLE 11

(8,9)-Benzo-3-carboxy-6-acetamido-octahydropyrollo[1,2-a]azepine-5-one

A solution of 0.99 g of aldehyde from Example 10 in 15.7 ml of ethanol was added gradually to a solution of 1.26 g of silver nitrate in 1.57 ml of water. To the well-stirred mixture there was added a solution of 0.94 g of potassium hydroxide in 15.7 ml of water. The resulting black suspension was stirred for 1.5 hours and then filtered through Supercel (a commercial diatomaceous earth filter). The filter cake was washed with water, the filtrate concentrated in vacuo to 15 ml, acidified with HCl, saturated with sodium chloride, and extracted three times with 25 ml portions of chloroform. The combined extracts were washed with brine, dried over magnesium sulfate, and concentrated to a solid residue. Trituration with ether-hexane furnished 0.87 g of crystalline solid. A sample was recrystallized from ethyl acetate for analysis.

Anal.: Calc'd for $C_{16}H_{18}N_2O_5$: C, 60.37; H, 5.70; N, 8.80. Found: C, 60.23; H, 5.70; N, 8.64.

Mass Spec., fast atom bombardment (FAB): (M+1)+ 319.

EXAMPLE 12

8,9-Benzo-3-carbomethoxy-6-amino-octahydropyrollo[1,2-a]azepine-5-one hydrochloride A mixture of 400 mg of the acid obtained in Example 11 and 4 ml of 31% HBr in glacial acetic acid was stirred until a solution was obtained which was then kept at room temperature overnight. This reaction mixture was concentrated in vacuo to a syrup which was freed from acetic acid and HBr by distilling four times with 10 ml portions of toluene. The residual dark violet solid was taken up in 10 ml of 3M HCl in methanol and kept at room temperature overnight. The solution was freed of solvent by distillation and the product isolated by trituration with ether containing a little isopropanol. Yield; 230 mg. Mass Spec., FAB: (M+1)+ 275. TLC and HPLC indicated that the material was essentially homogeneous. Infrared and NMR spectra were in accord with the proposed structure.

EXAMPLE 13

(8,9)-Benzo-3-carbomethoxy-6-(1-carbethoxy-3-phenylpropyl)amino-octahydropyrrollo[1,2-a]azepine-5-one.

The amino ester hydrochloride (230 mg, 0.74 mmole) obtained in Example 12 was converted to the free base by partitioning between aqueous sodium carbonate and chloroform, The chloroform solution was dried and concentrated to a glass (205 mg). The latter was dissolved in a solution of 760 mg (3.7 mmole) of ethyl 2-keto-4-phenylbutyrate, 4.5 ml of ethanol, and 45 mg of glacial acetic acid. To this solution, under nitrogen, there was added at a rate of 0.35 ml/hr. A solution of 140 mg of sodium cyanoborohydride (2.23 mmole) in 4.5 ml of ethanol. After stirring overnight, the reaction mixture was concentrated in vacuo to a syrup which was then partitioned betwen 5% aqueous sodium bicarbonate and ether. The ether extracts were washed with brine, dried and concentrated. The residual oil was chromatographed on 150 ml of silica gel, eluted with ethyl acetate-hexane (1:1). The fractions containing the desired product, as determined by TLC, IR and NMR, were combined. Yield; 250 mg. (72%). The spectral data (IR and NMR) were in accord with the proposed structure.

EXAMPLE 14

(8,9)-Benzo-3-carboxy-6-(1-carboxy-3-phenylpropyl)amino-octahydropyrrollo[1,2-a]azepine-5-one A mixture of 250 mg of the diester from Example 13, 4 ml of aqueous 0.5N NaOH, and 4 ml of methanol were stirred at room temperature overnight. The clear solution was concentrated in vacuo to ca. 3 ml. This concentrate was applied to a column of 120 ml of Dowex 502X, H+ resin and the column washed with 400 ml of water. The column was then eluted with 3% pyridine in water. The desired product appeared to eluate from 400 ml-600 ml. Yield; 167 mg (73%). The infrared spectrum was in accord with the proposed structure. Mass Spec. (M-H)+ 421. Inhibition of angiotensin converting enzyme; $I_{50}=3.9\times10^{-9}$. [A. A. Patchett, et al., Nature, 288, 280 (1980).]

What is claimed is:

1. A compound having the formula:

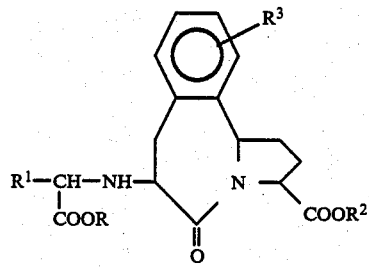

(I)

wherein:

R and $R^2$ are independently
 (a) hydrogen;
 (b) $C_1$-$C_6$-alkyl;
 (c) substituted $C_1$-$C_6$ alkyl wherein the substituents are hydroxy, $C_1$-$C_4$ alkyloxy and di-($C_1$-$C_4$)-alkylamino;
 (d) $C_6$ or $C_{10}$ aryl;
 (e) substituted $C_6$ or $C_{10}$ aryl wherein the substituents are $C_1$-$C_6$ alkyl, halo (F, Cl, Br, I), and $C_1$-$C_4$ alkyloxy;

$R^1$ is
 (a) hydrogen;
 (b) $C_1$-$C_8$ straight or branched alkyl;
 (c) $C_2$-$C_8$ straight or branched alkenyl;
 (d) $C_2$-$C_8$ straight or branched alkynyl;
 (e) $C_3$-$C_{10}$ cycloalkyl;
 (f) $C_6$ or $C_{10}$ aryl ($C_1$-$C_4$) alkyl;
 (g) substituted $C_1$-$C_8$ alkyl containing 1-3 substituents selected from halo (F, Br, Cl, I), carboxamido, $C_1$-$C_4$ alkoxy carbonyl, mercapto, amino, and R wherein R is as defined above;
 (h) $C_1$-$C_8$ alkyl optionally containing an O, S, S=O, O=S=O, C=O, $CONR_2$, $SO_2NR_2$, NRCO, $NRCONR_2$, $OCONR_2$, NRCOO or —$NR_2$ group wherein R is as defined above;

$R^3$ is
 (a) hydrogen;
 (b) halo (F, Br, Cl, I);
 (c) $C_1$-$C_6$ alkyl;
 (d) $C_1$-$C_6$ alkyloxy; and,
the pharmaceutically acceptable salts thereof.

2. The compound of claim 1 wherein:
R and $R^2$ are independently
 (a) hydrogen;
 (b) $C_1$-$C_6$ alkyl;
 (c) substituted $C_1$-$C_6$ alkyl wherein the substituents are hydroxy, $C_1$-$C_4$ alkyloxy and di-($C_1$-$C_4$)-alkylamino;

$R^1$ is
 (a) hydrogen;
 (b) $C_1$-$C_8$ straight or branched alkyl;
 (c) $C_2$-$C_8$ straight or branched alkenyl;
 (d) $C_2$-$C_8$ straight or branched alkynyl;
 (e) $C_3$-$C_{10}$ cycloalkyl;
 (f) $C_6$ or $C_{10}$ aryl ($C_1$-$C_4$) alkyl;
 (g) substituted $C_1$-$C_8$ alkyl containing 1-3 substituents selected from halo, carboxamido, $C_1$-$C_4$ alkoxy carbonyl, mercapto, amino, and R wherein R is as defined above;
 (h) $C_1$-$C_8$ alkyl optionally containing an O, S, C=O, $CONR_2$ or —$NR_2$ group wherein R is as defined above;

$R^3$ is
 (a) hydrogen;
 (b) halo (F, Br, Cl, I);
 (c) $C_1$-$C_6$ alkyl;
 (d) $C_1$-$C_6$ alkyloxy.

3. A compound which is a member of the group:
 (a) 7-(but-4-ene-yl)-5,6-benzperhydroazepine-2-one;
 (b) 7-(3,4-epoxybutyl)-5,6-benzperhydroazepine-2-one;
 (c) (8,9)-benzo-3-(benzyloxymethyl)-octahydropyrrollo[1,2-a]azepine-5-one;
 (d) (8,9)-benzo-3-(benzyloxymethyl)-6-(carbomethoxy)octahydropyrrollo[1,2-a]azepine-5-one;
 (e) (8,9)-benzo-3-(benzyloxymethyl)-6-(hydrazinocarbonyl)-octahydropyrrollo[1,2-a]azepine-5-one;
 (f) (8,9)-benzo-3-(benzyloxymethyl)-6-(acetamido)-2,3,4,5,8,9-hexahydropyrrollo[1,2-a]azepine-5-one;

(g) (8,9)-benzo-3-(hydroxymethyl)-6-(acetamido)-octahydropyrrollo[1,2-a]azepine-5-one;

(h) (8,9)-benzo-3-formyl-6-(acetamido)-octahydropyrollo[1,2-a]azepine-5-one;

(i) (8,9)-benzo-3-carboxy-6-acetamido-octahydropyrrollo[1,2-a]azepine-5-one;

(j) (8,9)-benzo-3-carbomethoxy-6-amino-octahydropyrrollo[1,2-a]azepine-5-one hydrochloride; and, (k) (8,9)-benzo-3-carbomethoxy-6-(1-carboethoxy-3-phenylpropyl)amino-octahydropyrrollo[1,2-a]-azepine-5-one.

4. A pharmaceutical composition useful in the treatment of hypertension which comprises a pharmaceutically acceptable carrier and an antihypertensively effective amount of compound of claim 1.

5. The composition of claim 4 which includes another antihypertensive and/or a diuretic and/or calcium entry blocker compound selected from the group: acetazolamide, amiloride, aminophylline, atenolol, bendroflumethiazide, benzthiazide, bumetanide, chorothalidone, chlorothiazide, clonidine, cryptenamine acetates and cryptenamine tannates, cyclothiazide, deserpidine, diazoxide, diltiazem, (S)-1-[[2-(3,4-dimethoxyphenyl)-ethyl]amino]-3-[4-(2-thienyl)-1H-imidazol-2-yl]-phenoxy]-2-propanol, ethacrynic acid, flumethiazide, furosemide, guanethidene sulfate, hydralazine hydrochloride, hydrochlorothiazide, hydroflumethiazide, (+)-4-[3-[-[2-(1-hydroxycyclohexyl) ethyl]-4-oxo-2-thiazolidinyl]propyl]-benzoic acid, indacrinone and variable ratios of its enantiomers, merethoxylline procaine, methylclothiazide, methyldopa, methldopate hydrochloride, metolazone, metoprolol tartate, minoxidil, naldolol, nifedipine, pargyline hydrochloride, pindolol, polythiazide, prazosin, propranolol, quinethazone, *rauwolfia serpentina,* rescinnamine, reserpine, sodium ethacrynate, sodium nitroprusside, spironolactone, ticrynafen, timolol, triamterene, trichlormethiazide, trimethophan camsylate, bepridil, diltiazim, etafenone, falipamil, felodipine, flunarizine, gallopamil, indapamide, lidoflazine, nicardipine, nifedipine, nimopidine, nitrendipine, perhexiline, prenylamine, tiapamil, verapamil, as well as admixtures and combinations thereof.

6. A method of treating hypertension which comprises administering to a patient in need of such treatment an antihypertensively effective amount of a compound of claim 1.

7. A process for preparing a compound having the formula:

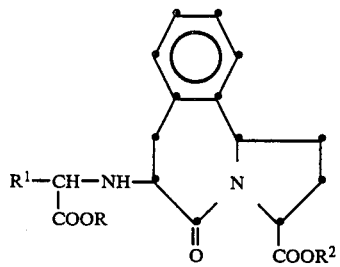

I wherein R, $R^1$ and $R^2$ are as defined in claim 1, which process comprises hydrolyzing a compound having the formula:

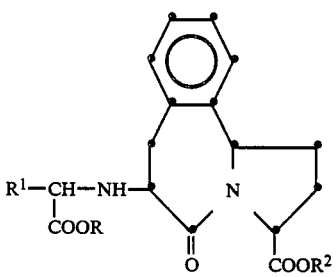

XIX wherein $R^1$ and $R^2$ are as defined in claim 1 and R is an alkyl of an ester group, in the presence of a base to obtain said Formula I compound.

8. A compound which is a member of the group:
(a) 1-(but-3-ene-yl)-2-tetralone; and,
(b) 1-(but-3-ene-yl)-2-oximino-tetralin.

* * * * *